US007002044B2

(12) United States Patent
Erkey et al.

(10) Patent No.: US 7,002,044 B2
(45) Date of Patent: Feb. 21, 2006

(54) CATALYSIS BY WATER-SOLUBLE ORGANOMETALLIC COMPLEXES IN WATER-IN-DENSIFIED FLUID MICROEMULSIONS

(75) Inventors: Can Erkey, South Windsor, CT (US); Xing Dong, Willimantic, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 10/641,705

(22) Filed: Aug. 15, 2003

(65) Prior Publication Data

US 2004/0097761 A1    May 20, 2004

Related U.S. Application Data

(60) Provisional application No. 60/403,700, filed on Aug. 15, 2002.

(51) Int. Cl.
*C07C 45/50*    (2006.01)
(52) U.S. Cl. .................. 568/429; 568/444; 568/451; 568/452
(58) Field of Classification Search ............... 568/429, 568/444, 451, 452
See application file for complete search history.

(56) References Cited

U.S. PATENT DOCUMENTS

| 4,933,404 | A | 6/1990 | Beckman et al. ............ 526/207 |
| 4,996,366 | A | 2/1991 | Tinucci et al. ............... 568/454 |
| 5,158,704 | A | 10/1992 | Fulton et al. ................ 252/309 |
| 5,238,671 | A | 8/1993 | Matson et al. ............... 423/397 |
| 5,266,205 | A | 11/1993 | Fulton et al. ................ 210/639 |
| 5,770,172 | A | 6/1998 | Linehan et al. ........... 423/561.1 |
| 5,814,678 | A | 9/1998 | Randolph ..................... 522/18 |
| 6,299,652 | B1 | 10/2001 | Jureller et al. ................. 8/142 |
| 6,452,055 | B1 | 9/2002 | Koch et al. .................. 568/454 |
| 6,479,708 | B1 * | 11/2002 | Jacobson et al. ............ 568/451 |
| 2002/0070167 | A1 | 6/2002 | Krasutsky et al. .......... 210/634 |

OTHER PUBLICATIONS

Niemeyer et al. The pH within PFPE Reverse Micelles Formed in Supercritical CO2.□□Journal of Physical Chemistry B, 1998; 102, pp. 1474-1478.*
Hoefling et al. Microemulsions in Near-Critical and Supercritical CO2. Journal of Physical Chemistry. 1991, vol. 95, pp. 7127-7129.*
WO9961401; A1; 19991202 (Abstract Only).
Smith, R. T. et al., "Rhodium Complexes of the Water-Soluble Phosphine Ph2PCH2CH2NMe3+, Their Complexes with Hydride, Olefin, and Carbon Monoxide Ligands. Their Use as Olefin Hydrogenation and Hydroformylation Catalysts in Aqueous Solution and in Aqueous/Organic Solven Two-Phase Systems and Adsorbed on A Cation-Exchange Resin", Organometallics, 1983, 2, 1138-1144.

Hou, M-J. et al., "Effects of the Molecular Structure of the Interface and Continuous Phase on Solubilization of Water in Water/Oil Microemulsions", Langmuir 1987, 3, 1086-1096.
Arhancet, J. P. et al., .Hydroformulation by supported aqueous-phase catalysis: a new class of heterogeneous catalysts, Nature, 339 (1989), 454-455.
Wan et al., "Design and Synthesis of a Heterogeneous Asymmetric Catalyst", Nature, vol. 370 (1994), 449-450.
Harrison, K. L. et al., "Effect of Surfactants on the Interfacial Tension Between Supercritical Carbon Dioxide and Polyethylene Glycol", Langmuir, 1996, 12, 2637-2644.
Johnston, K. P. et al., "Water-In-Carbon Dioxide Microemulsions: An Environment for Hydrophiles Including Proteins", Science, vol. 271, (1996), 624-626.
Kragl et al., "Membrane Reactors in Homogeneous Catalysis", Appl. Homogeneous Catal. Organomet. Compd. 1996, vol. 2, 832-843.
Clarke, M. J. et al., "Water in Supercritical Carbon Dioxide Microemulsions: Spectroscopic Investigation of a New Environment for Aqueous Inorganic Chemistry", J. Am. Chem. Soc. 1997, 119, 6399-6406.
Desphande, R. M. et al., "Effect of pH on rate and selectivity behavior in biphasic hydroformulation of 1-octene", Journal of Molecular Catalysis A: Chemical 126 (1997) 133-140.
Hietz, M. P. et al., "Water Core within Perfluoropolyether-Based Microemulsions Formed in Supercritical Carbon Dioxide", J. Phys. Chem B 1997, 101, 6707-6714.
Cornils, B. et al., "Aqueous-Phase Organometallic Catalysis; Concepts and Applications", 1998, Weinhem, Germany: Wiley-VCH, 59-143.
Horvath, I. T., "Fluorous Biphase Chemistry", Acc. Chem. Res. 1998, 31, 10, 641-650.
Niemeyer, E. D., "The pH within PFPE Reverse Micelles Formed in Supercritical CO2", J. Phys. Chem. B 1998, 102, pp. 1474-1478.
Cornils, B., "Bulk and Fine Chemicals Via Aqueous Biphasic Catalysis", Journal of Molecular Catalysis A: Chemical 143 (1999) 1-10.
Holmes, J. D. "Synthesis of Cadmium Sulfide Q Particles in Water-in-CO2 Microemulsions", Langmuir 1999, 15, 6613-6615.
Holmes, J.D. "Buffering the Aqueous Phase pH in Water-in-CO2 Microemulsions", J. Phys. Chem. B 1999, 103, 5703-5711.
Jacobson, G. B., "Organic Synthesis in Water/Carbon Dioxide Microemulsions", J. Org. Chem. 1999, 64, 1201-1206.

(Continued)

*Primary Examiner*—Sikarl A. Witherspoon
(74) *Attorney, Agent, or Firm*—Cantor Colburn LLP

(57) ABSTRACT

A microemulsion containing water, a densified fluid, a surfactant, and an organometallic catalyst is used to catalyze chemical reactions. The organometallic catalyst preferably has substantial solubility in the water phase of the microemulsion. Separation of reaction products from the microemulsion is facilitated by removal of the densified fluid.

41 Claims, 2 Drawing Sheets

OTHER PUBLICATIONS

Jacobson, G. B., "Enhanced Catalyst Reactivity and Separations Using Water/Carbon Dioxide Emulsions", J. Am. Chem. Soc. 1999, 121, 11902-11903.

Kane, M. A., "Performance of Cholesterol Oxidase Sequestered within Reverse Micelles Formed in Supercritical Carbon Dioxide", Langmuir 2000, 16, 4901-4905.

Liu, Z. et al.., "Water in Carbon Dioxide Microemulsions with Fluorinated Analogues of AOT", Langmuir 2001, 17, 274-277.

Dong, X. et al., "Behavior and Micelle Size of an Aqueous Microdispersion in Supercritical CO2 with a Novel Surfactant", Ind. Eng. Chem. Res. 2002, 41, 1038-1042.

X. Dong et al., "Synthesis of CuS Nanoparticles in Water-in-Carbon Dioxide Microemulsions", Ind. Eng. Chem. Res. 2002, 41, 4489-4493.

Can Erkey et al., "Hydroformylation of ethylene in supercritical carbon dioxide using Ruc(SO)12 as a catalyst precursor", Catalysis Communications 3 (2002) 213-219.

Shaker Haji et al., "Investigation of rhodium catalyzed hydroformulation of ethylene in supercritical carbon dioxide by in situ FTIR spectroscopy", Tetrahedron, vol. 58 (2002) 3929-3941.

Haumann,, M. et al., "Hydroformylation of 1-dodecene using Rh-TPPTS in a microemulsion", Applied Catalysis A: General 225 (2002) 239-249.

Ohde, H. et al., "Water-in-CO2 Microemulsions as Nanoreactors for Synthesizing CdS and ZnS Nanoparticles in Supercritical CO2", Nano Letters 2002, vol. 2, No. 7, pp. 721-724.

Ohde, H. et al., "Hydrogenation of Olefins in Supercritical CO2, Catalyzed by Palladium Nanoparticles in a Water-in-CO2 Microemulsion", J. Am. Chem. Soc., 2002, 124, 4540-4541.

http://www.cmt.anl.gov/toroid-cavity/poster1/aip-04index.html ; printed Aug. 5, 2002; 18 pages.

Keith P. Johmston et al., "Reactions and Synthesis in Microemulsions and Emulsions in Carbon Dioxide", Surfactant Synthesis Series (2001), 100 (Reactions and Synthesis in Surfactant Systems), 349-358.

David E. Fremgen et al., "Microemulsions of water in superficial carbon dioxide: an in-situ NMR investigation of micelle formation and structure" Journal of Supercritical Fluids 19 (2001) 287-298.

Gunilla B. Jacobson et al., "Biphasic Catalysis in Water/Carbon Dioxide Micellar Systems", (Abstract Only), American Chemical Society, 217th ACS National Meeting 0-8412-3672-0, Mar. 21-25, 1999.

J. D. Holmes et al., "Bioconversions in a Water-in-CO2 Microemulsion", Langmuir, vol. 14, No. 22, 1998, 6371-6376.

Yutaka Ikushima, "Supercritical fluids: an interesting medium for chemical and biochemical processes", Advances in Colloid and Interface Science 71-72 (1997) 259-280.

Marina A. Hauck et al., "Hemoproteins-Catalyzed Oxidations of Organosulfur Compounds in Reverse Micelles, Microemulsions, and Emulsions in Supercritical Fluids", (Abstract Only), American Chemical Society, 222nd ACS National Meeting 0-8412-3803-0, Aug. 26-30, 2001.

Dongil Lee et al., "Electrochemistry In Water-In-Supercritical-CO2, Microemulsions", (Abstract Only) American Chemical Society, 222nd ACS National Meeting 0-8412-3803-0, Aug. 26-30, 2001.

Robert H. Grubbs et al., "Catalytic Reduction of Olefins with a Polymer-Supported Rhodium(I) Catalyst" Journal of the American Chemical Society, 93:12, Jun. 16, 1971, pp. 3062-3063.

M. Capka et al., "Hydrogenation, Hydrosilylation and Hydroformylation of Olefins Catalysed by Polymer-Supported Rhodium Complexes", Tetrahedron Letters No. 50, pp. 4787-4790, 1971.

Yutaka Ikushima, "Supercritical fluids as media for chemical and biochemical reactions", Recent Research Developments in Chemical Engineering (1997), 1, 49-57.

* cited by examiner

CATALYSIS BY WATER-SOLUBLE ORGANOMETALLIC COMPLEXES IN WATER-IN-DENSIFIED FLUID MICROEMULSIONS

CROSS REFERENCE TO RELATED APPLICATIONS

This application claims priority to U.S. Provisional Application Ser. No. 60/403,700, filed Aug. 15, 2002.

BACKGROUND

There is a growing demand for highly selective and efficient catalytic processes due to today's economical and environmental constraints in the chemical industries. Organometallic homogeneous catalysts seem ideally suited to answer this challenge since they offer higher activity and chemo-, regio-, and stereo-selectivity than their heterogeneous counterparts for a wide variety of reactions. In spite of these favorable properties, the number of homogeneous catalytic processes operating on an industrial scale is small. This has primarily been due to lack of efficient methods to recover expensive homogeneous catalysts from reaction mixtures and to recycle them.

Recovery and recycling of homogeneous catalysts is an active research area and a variety of methods are currently being investigated in many laboratories around the world. Among these, the use of aqueous biphasic catalysis is a very promising method and has been practiced on an industrial scale for production of n-butyraldehyde by hydroformylation of propylene. However, the low solubilities of most organic compounds in water may be prohibitive in extension of this technology to more hydrophobic reactants. Furthermore, a biphasic system is not preferable for reactions that are controlled by mass transfer.

There remains a need for homogeneous catalysis methods that provide ease of catalyst recovery and reuse, rapid mass transfer, and efficient conversion of reactants of various hydrophobicities.

BRIEF SUMMARY

The above-described and other drawbacks and disadvantages of the prior art are alleviated by a catalytic process, comprising: reacting a reactant with an organometallic catalyst to form a product in a microemulsion comprising the reactant and the organometallic catalyst, and further comprising water, a densified fluid, and a surfactant; and separating the product from the microemulsion.

Other embodiments, including batch and continuous catalysis methods utilizing an organometallic catalyst in a water-in-densified fluid microemulsion, are described in detail below.

DETAILED DESCRIPTION OF THE PREFERRED EMBODIMENTS

Figure 1:
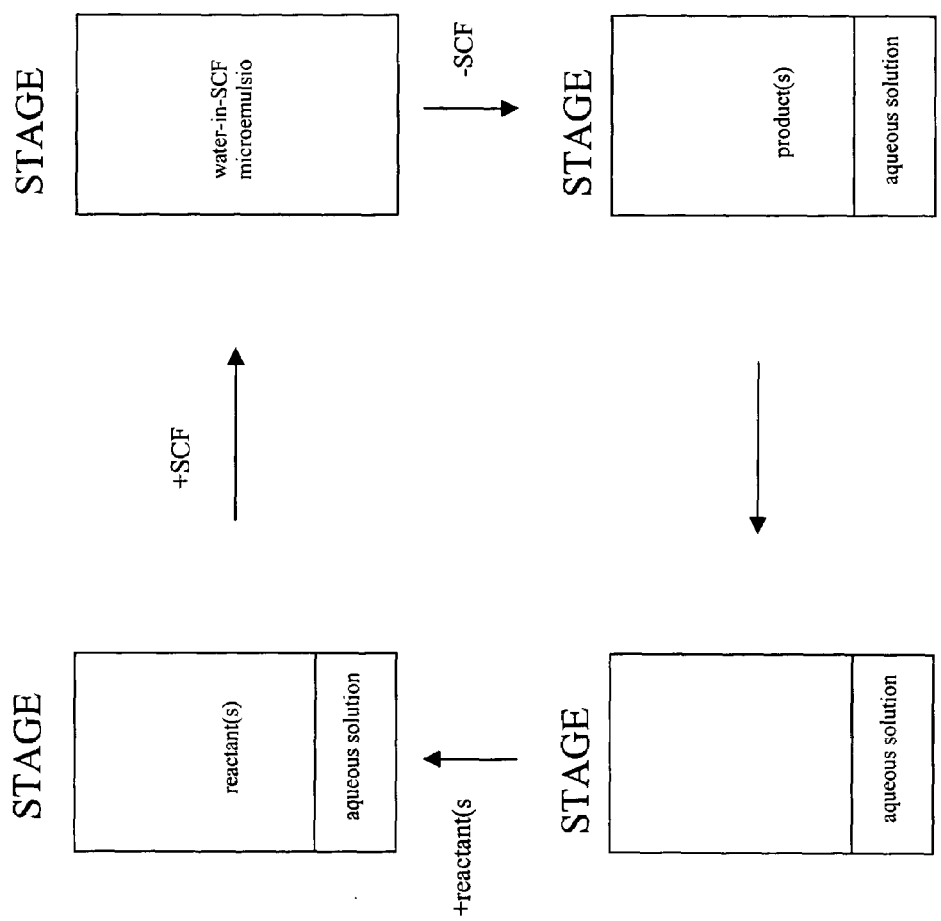
FIG. 1 is a simplified process diagram of a microemulsion catalysis method including catalyst recycling and simple product recovery.

One embodiment is a catalytic process, comprising: reacting a reactant with an organometallic catalyst to form a product in a microemulsion comprising the reactant and the organometallic catalyst, and further comprising water, a densified fluid, and a surfactant; and separating the product from the microemulsion.

A densified fluid is a fluid having a density greater than its density at 25° C. and 1 atmosphere. The densified fluid may be a gas, a liquid, or, preferably, a supercritical fluid. A supercritical fluid is a substance above its critical temperature and critical pressure. Supercritical fluids have both gas- and liquid-like properties. In one embodiment, the supercritical fluid has a critical temperature less than or equal to about 31° C. In another embodiment, the supercritical fluid has a critical pressure less than or equal to about 7.4 megapascals. Suitable densified fluids include, for example, carbon dioxide, ethane, propane, ethylene, propylene, nitrous oxide, xenon, ammonia, fluoroform, water, and the like, and mixtures thereof. Critical temperatures ($T_c$) and critical pressures ($p_c$) for some of these fluids are given below.

| fluid | $T_c$ (K) | $p_c$ (bar) |
|---|---|---|
| Carbon dioxide | 304 | 74 |
| Water | 647 | 221 |
| Ethane | 305 | 49 |
| Ethylene | 282 | 50 |
| Propane | 370 | 43 |
| Xenon | 290 | 58 |
| Ammonia | 406 | 114 |
| Nitrous oxide | 310 | 72 |
| Fluoroform | 299 | 49 |

In a preferred embodiment, the densified fluid comprises carbon dioxide. When the densified fluid is a supercritical fluid, it may be added to or removed from the reactor in a non-supercritical state, e.g., as a gas or liquid.

The method is particularly useful for catalyzing reactions involving gaseous reactants. Thus, the reactant may comprise a compound that is a gas at 25° C. and one atmosphere. In one embodiment, the method comprises catalysis of a reaction of carbon monoxide, hydrogen, or a mixture thereof.

The method is also useful for catalyzing reactions of reactants that are liquids at 25° C. and one atmosphere. For example, the reactant may comprise olefinic unsaturation. In one embodiment, the reactants comprise both gaseous and liquid reactants. For example, the method may comprise catalysis of a hydroformylation reaction in which a liquid olefin, carbon monoxide, and molecular hydrogen are reactants. The chemical reaction for hydroformylation of a generic alpha-olefin $RCH=CH_2$ is given in equation (I):

$$RCH=CH_2 + H_2 + CO \rightarrow RCH_2CH_2C(O)H \qquad (I)$$

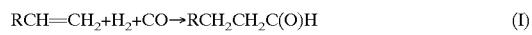

Other reaction types that may be catalyzed by the method include, for example, hydrogenation, hydrohalogenation, halogenation, oxidation including hydrocarbon oxidation, carbonylation, decarbonylation, carboxylation, decarboxylation, hydrodimerization, isomerization including olefin isomerization, olefin metathesis, hydrosilylation, hydrocyanation, electrophilic aromatic substitution, arene-olefin coupling, arene-arene coupling, esterification, oligomerization, polymerization, asymmetric arylation, asymmetric allylation, asymmetric hydrogenation, asymmetric hydroformylation, and the like. Such reactions are described, for example, in Parshall, G. W. and Ittel, S. D., "Homogeneous Catalysis;

The Applications and Chemistry of Catalysis by Soluble Transition Metal Complexes", 1992, New York: Wiley-Interscience.

The method is also useful for catalyzing reactions of reactants that are solids at 25° C. and one atmosphere. For example, the method is useful for hydrogenation of solid such as, for example, tiglic acid.

The water-in-densified fluid (W/DF) microemulsion comprises water, a densified fluid, and a surfactant. The microemulsion may comprise a continuous phase comprising the densified fluid and a dispersed phase comprising water and surfactant. Suitable surfactants generally have two kinds of groups, one densified-fluid-philic and one hydrophilic. Surfactants suitable for supporting water-in-densified fluid microemulsions are known and include, for example, the perhalogenated surfactants, propylene glycol surfactants, perhaloether surfactants, and polydimethylsiloxane surfactants described in U.S. Pat. No. 6,299,652 B1 to Jureller et al.

In a preferred embodiment, the surfactant may comprise a salt of a fluorinated poly(ether)carboxylate or a fluorinated poly(ether)sulfonate. Cations employed in the salts may include, for example, alkali metals, alkaline earth metals, substituted or unsubstituted ammonium ions, substituted or unsubstituted phosphonium ions, and the like, and combinations thereof. In a preferred embodiment, the surfactant comprises a sodium bis(perfluoro-$C_4$-$C_{12}$-alkyl)-2-sulfosuccinate, such as, for example, sodium bis(3,3,4,4,5,5,6,5,7,7,8,8,8-tridecafluorooctyl)-2-sulfosuccinate, sodium bis(2,2,3,3,4,4,5,5-octafluoro-1-pentyl)-2-sulfosuccinate, sodium bis(2,2,3,4,4,4-hexafluorobutyl)-2-sulfosuccinate, or a mixture thereof. In another embodiment, the surfactant comprises a the surfactant comprises a fluorinated analog of sodium bis(2ethylhexyl)-2-sulfosuccinate in which at least one hydrogen atom is replaced by a fluorine atom. For example, each of the two 2-ethylhexyl groups may independently be partially fluorinated or perfluorinated. Syntheses of these fluorinated surfactants are known in the literature. See, for example, Z. Liu and C. Erkey, *Langmuir* 2001, 17(2), 274–277; and X. Dong, C. Erkey, H. Dai, H. Li, H. D. Cochran, and J. S. Lin, *Ind. Eng. Chem. Res.* 2002, 41(5), 1038–1042.

The microemulsion may preferably comprise dispersed phase (aqueous) droplets having an average particle size less than or equal to 100 nanometers, preferably less than or equal to 50 nanometers, more preferably less than or equal to 20 nanometers, still more preferably less than or equal to 10 nanometers, even more preferably less than or equal to 5 nanometers. Smaller emulsion particles promote greater mass transport in the microemulsion.

In one embodiment, the microemulsion comprises at least 1 weight percent water, preferably at least 2 weight percent water, more preferably at least 4 weight percent water, even more preferably at least 6 weight percent water, based on the total weight of the microemulsion.

As demonstrated in the Examples below, the present inventors have found that when the densified fluid is carbon dioxide, reaction rates may be enhanced by the addition of a base to the aqueous phase. This added base serves to counteract the effect of dissolved carbon dioxide (i.e., carbonic acid) and may therefore be used to adjust the pH of the carbonate-buffered aqueous phase. Thus, in one embodiment, the microemulsion has a pH of about 2 to about 8. Within this range, it may be preferred that the pH is at least about 3, more preferably at least about 4. Also within this range, it may be preferred that the pH is up to about 7, more preferably up to about 6. Methods of measuring pH in water-in-carbon dioxide microemulsions are described, for example, in E. D. Niemeyer et al., *J. Phys. Chem. B* 1998, volume 102, number 8, pages 1474–1478; and J. D. Holmes et al. *Journal of Physical Chemistry B* 1999, volume 103, number 27, pages 5703–5711.

The method may, optionally, further comprise add adding a solvent to the reactor. For example, the aqueous dispersed phase may further include a solvent having a water solubility of at least 1 g/L, such as a lower alkanol such as methanol, ethanol, or the like. Alternatively, the densified continuous phase may further include an organic solvent with a water solubility less than 0.1 g/L, such as, for example, an aliphatic solvent such as cyclohexane, or an aromatic solvent such as toluene. However, product recovery may be facilitated by omitting such an additional solvent.

The method comprises reacting a reactant with an organometallic catalyst to form a product. The organometallic complex comprises a metal and an organic ligand. The organic ligand preferably has at least one carbon atom bound to at least one hydrogen atom. The complex may be preformed or formed in situ from one or more precursors. For example, the organometallic complex may be formed from a metal complex precursor with one or more labile ligands plus an excess of a catalyst ligand.

In a preferred embodiment, the organometallic catalyst has sufficient water solubility to partition primarily into the dispersed phase. In other words, it may be preferred that, under reaction conditions, at least about 50% of the organometallic catalyst resides in the dispersed phase. It is therefore preferred to employ an organometallic catalyst having a water solubility of at least about 0.001 gram per liter (g/L) at 25° C. and one atmosphere, preferably at least about 0.01 g/L, more preferably at least about 0.1 g/L, even more preferably at least about 1 g/L. Although the organometallic catalyst may preferably have a substantial water solubility, it will be understood that the catalyze reaction may occur in the densified fluid phase or the densified fluid-water interface, as well as in the aqueous phase.

There is no particular limit on the metal of the organometallic complex. For example, the organometallic catalyst may comprise Mg, Al, Ca, Sc, Ti, V, Cr, Mn, Fe, Co, Ni, Cu, Zn, Ga, Ge, Sr, Y, Zr, Nb, Mo, Tc, Ru, Rh, Pd, Ag, Cd, In, Sn, Ba, La, Ce, Pr, Nd, Pm, Sm, Eu, Gd, Tb, Dy, Ho, Er, Tm, Yb, Lu, Hf, Ta, W, Re, Os, Ir, Pt, Au, Hg, Tl, Pb, Ra, Ac, Th, Pa, U, or a combination thereof. The organometallic catalyst may preferably comprise Y, Zr, Nb, Mo, Tc, Ru, Rh, Pd, Ag, La, Hf, Ta, W, Re, Os, Ir, Pt, Au, or a combination thereof. In a presently preferred embodiment, the organometallic catalyst comprises rhodium.

The water-solubility of the organometallic catalyst may be increased by the use of water-soluble ligands. For example, the organometallic catalyst may comprise a phosphine ligand having a water solubility of at least about 0.1 g/L at 25° C. and one atmosphere, preferably at least about 1 g/L, more preferably at least about 10 g/L. Many suitable ligand types and specific ligands are described, for example, in Boy Cornils and Wolfgang A. Herrmann, Eds., "Aqueous-Phase Organometallic Catalysis; Concepts and Applications", 1998, Weinheim, Germany: Wiley-VCH, pages 59–143. Such ligands generally include at least one water-solubilizing group, such as a sulfonic acid or sulfonate salt, a carboxylic acid or carboxylate salt, a phoshonic acid or phosphate salt, a hydroxyl group or hydroxide salt, an unsubstituted amino group or unsubstituted ammonium salt, a substituted amino group or substituted ammonium salt, a repeating alkylene oxy group, or the like. Examples of water soluble ligands include, for example, sulfonated aryl phosphines, trialkylammoniumalkyl phosphines, phosphines containing carboxylated aromatic groups and/or side chains, phosphines containing carboxyalkyl groups (both free acids and salts), hydroxyalkyl-substituted phosphines, trialkylammoniumalkyl-substituted phosphines, phosphines containing phosphonated aromatic groups and/or side chains, carboxy-substituted bipyridines, sulfonate-substituted bipyridines, sulfonated chiral phosphines, carboxy-substituted cyclopentadienes, and the like, and mixtures thereof.

It will be understood that throughout this application, unless otherwise specified, "alkyl" is defined as $C_1$–$C_{12}$ alkyl; "aryl" is defined as $C_6$–$C_{18}$ aryl; "alkylene" is defined as $C_2$–$C_{12}$ alkylene; and halogen is defined as F, Cl, Br, I, or At.

A presently preferred phosphine ligand is 3,3',3"-phosphinidynetris(benzenesulfonic acid), trisodium salt (TPPTS), which may be prepared according to known methods or purchased commercially from, for example, Aldrich Chemical Company.

The organometallic catalyst need not include a water-soluble ligand to have water solubility. For example, the organometallic catalyst may be inherently water-soluble by virtue, for example, of its ionic nature. Intrinsically water-soluble metal complexes are described, for example, on pages 65–68 of Cornils and Hermann, cited above.

In one embodiment, the organometallic catalyst has a molecular weight less than or equal to 5,000 atomic mass units (AMU), preferably less than or equal to 4,000 AMU, more preferably less than or equal to 3,000 AMU, still more preferably less than 2,000 AMU.

In another embodiment, the organometallic catalyst has a molecular weight greater than 5,000 AMU. For example, the organometallic catalyst may comprise a phosphonated polystyrene and ligated rhodium or platinum atoms (see, for example, P. Kalck and M. Dessoudeix, in B. Cornils and W. A. Herrmann, Eds., "Aqueous-Phase Organometallic Catalysis", 1998, Weinheim: Wiley-VCH, pages 113–119; R. H. Grubbs, L. C. Croll, *J. Am. Chem. Soc.* 1971, 93, 3062; J. P. Collmann, L. J. Hegedus, M. P. Cook, J. R. Norton, G. Dolcetti, D. N. Marquardt, *J. Am. Chem. Soc.* 1972, 117, 1789; and M. Capka, P. Svoboda, M. Creny, and J. Hetflejs, *Tetrahedron Lett.* 1971, 4787).

The method may be carried out in batch or continuous mode. For example, a batch mode method may comprise: adding a reactant to a reactor containing water, an organometallic catalyst, and a surfactant; adding a fluid to the reactor, wherein the fluid is capable of forming a densified fluid; forming a water-in-densified fluid microemulsion in the reactor, wherein the microemulsion facilitates a catalyzed reaction of the reactant to form a product; removing densified fluid from the reactor; and removing product from the reactor. As mentioned above, "removing densified fluid from the reactor" includes removing the fluid in its supercritical or liquid or gaseous state. It will understood that "facilitates a catalyzed reaction" means that the rate of conversion of reactant per unit catalyst is greater (preferably at least ten times greater, more preferably at least 100 time greater) after formation of the microemulsion than before formation of the microemulsion.

Another embodiment of the method is a multi-cycle batch mode comprising: (1) charging a reactor with water, an organometallic catalyst, and a surfactant; (2) adding a reactant to the reactor; (3) adding a fluid to the reactor, wherein the fluid is capable of forming a densified fluid; (4) forming a water-in-densified fluid microemulsion in the reactor, wherein the microemulsion facilitates a catalyzed reaction of the reactant to form a product; (5) removing carbon dioxide from the reactor; (6) removing the product from the reactor; and (7) repeating steps (2) to (6).

In a preferred embodiment, the catalytic process comprises: reacting an olefin, hydrogen, carbon monoxide, and an organometallic catalyst comprising rhodium and trisodium 3,3',3"-phosphinidynetris(benzenesulfonate) in a microemulsion further comprising water, a densified fluid, and a surfactant to form a hydroformylation product; and separating the hydroformylation product from the microemulsion.

One embodiment is illustrated in the simplified process diagram of FIG. 1. In STAGE 1, an aqueous solution (containing water, an organometallic catalyst at least partially dissolved in water, and surfactants) and reactant(s) are fed to a reactor. Subsequently, the reactor is charged with densified fluid (which may be in gaseous, liquid, or supercritical state) and the temperature and/or pressure are adjusted to yield the water-in-densified fluid microemulsion. Catalysis takes place in STAGE 2 in the water-densified fluid microemulsion. The contents of the reactor may be cooled and the densified fluid is vented once the reaction has been reached the desired conversion. Reduction of pressure causes the microemulsion to breakdown. Consequently, the system separates into an aqueous phase and an organic (product(s)) phase as shown in STAGE 3. The product(s) are easily removed by phase separation, leaving the aqueous solution containing the surfactant and the organometallic catalyst. The reactor is subsequently charged with the gaseous and liquids reactant(s) once again to restart the cycle. The breakdown of the microemulsion at the end of STAGE 2 by simple pressure reduction is an important advantage of densified fluids.

The invention is further illustrated by the following non-limiting examples.

EXAMPLES 1–5

These examples describe hydroformylation reactions carried out in water-carbon dioxide microemulsions supported by the sodium salt of bis(2,2,3,3,4,4,5,5-octafluoro-1-pentyl)-2-sulfosuccinate (di-HCF4). The synthesis procedure for this surfactant and the properties of such microemulsions are reported in Z. Liu and C. Erkey, *Langmuir* 2001, 17(2), 274–277; and X. Dong, C. Erkey, H. Dai, H. Li, H. D. Cochran, and J. S. Lin, *Ind. Eng. Chem. Res.* 2002, 41(5), 1038–1042.

The organometallic catalyst used in these examples is believed to be Rh(H)(CO)(TPPTS)$_2$ formed in situ from hydrogen, the catalyst metal precursor dicarbonyl rhodium acetylacetonate (Rh(CO)$_2$acac), and the water-soluble ligand 3,3',3"-phosphinidynetris(benzenesulfonic acid) trisodium salt (TPPTS), wherein Rh(CO)$_2$acac and TPPTS are added in a 1:4 molar ratio.

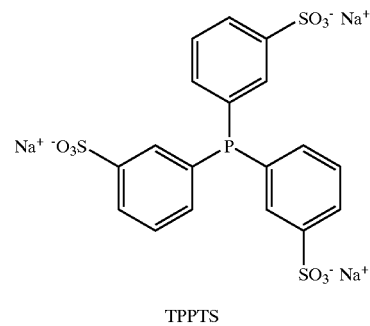

TPPTS

The catalyst concentration was 0.01 mole per liter of aqueous phase based on rhodium. A typical run used 0.01 millimole Rh(CO)$_2$acac, 0.04 millimole TPPTS, 0.2 milliliters olefin, 1 milliliter (0.056 mmol) water or 0.25 mole/liter sodium hydroxide solution, 0.56 mmol di-HCF4, and 200 pounds per square inch absolute (psia) synthesis gas (carbon monoxide and hydrogen in a 1:1 molar ratio).

Experiments were conducted batch-wise in a custom-manufactured reactor (internal volume of 54 milliliters), which was manufactured from stainless steel 316 and was equipped with two sapphire windows (diameter=1.25 inch, thickness=0.5 inch). The windows were sealed on both sides with polyetheretherketone seals. In a typical experiment, desired amounts of di-HCF4 surfactant, catalyst metal precursor, catalyst ligand(s), water, olefin, and a magnetic stir bar were placed in the vessel, which was then sealed. The vessel was then placed on a magnetic stir plate and air was removed air from the vessel by flushing it with synthesis gas. Then the reactor was charged with a desired amount of synthesis gas and carbon dioxide. The reactor was heated to the desired temperature by a recirculation heater/cooler (Fischer) via a machined internal coil. The vessel was charged with $CO_2$ from a syringe pump (ISCO, 100D) equipped with a cooling jacket. The microemulsion formed by self-assembly with minimal agitation. The temperature was controlled during each experiment to within 0.5° C. The pressure was adjusted with a syringe pump and measured using a pressure transducer (Omega Engineering Inc, PX01K1-5KGV). In all cases, the solutions became clear and yellow after a period of 10 minutes, which indicated the formation of the microemulsion with the catalyst formed in situ inside the water droplets. The solutions were clear and homogeneous during the entire run. The results are summarized in Table 1.

The data show, first, that reaction rates were higher when 0.25 M NaOH is used in place of water. The data show, second, that the reaction rates were relatively insensitive the solubilities of olefins in water: the solubility of 1-pentene is over 50 times higher than that of 1-octene in bulk water, but the reaction rate for 1-pentene is only two times higher than that of 1-octene. While not wishing to be bound by any particular hypothesis, the inventors believe that the reactions might occur mainly in the interface between the aqueous and densified fluid phases, which suggests the feasibility of catalyzed reactions on reactants having extremely low water solubilities.

TABLE 1

| Ex. | Olefin | Aqueous Solvent | Temperature (° C.) | Time (Hours) | Conversion (%) | Selectivity |
| --- | --- | --- | --- | --- | --- | --- |
| 1 | 1-octene | water | 87.1 | 43 | 6 | 1.6* |
| 2 | 1-pentene | water | 85.7 | 43 | 13 | n.d.** |
| 3 | ethyl acrylate | water | 85.2 | 22 | 24 | *** |
| 4 | 1-pentene | 0.25 M NaOH | 66.5 | 40 | 36 | 2.3 |
| 5 | Ethyl acrylate | 0.25 M NaOH | 65.1 | 22 | 75 | 2.3 |

*selectivity calculated as the ratio of linear:branched
**n.d. = not determined
***For ethyl acrylate hydroformylation, the selectivity is defined by the ratio of aldehyde to enol formed. Under this reaction condition, no enol form was found.

EXAMPLE 6

Figure 2:
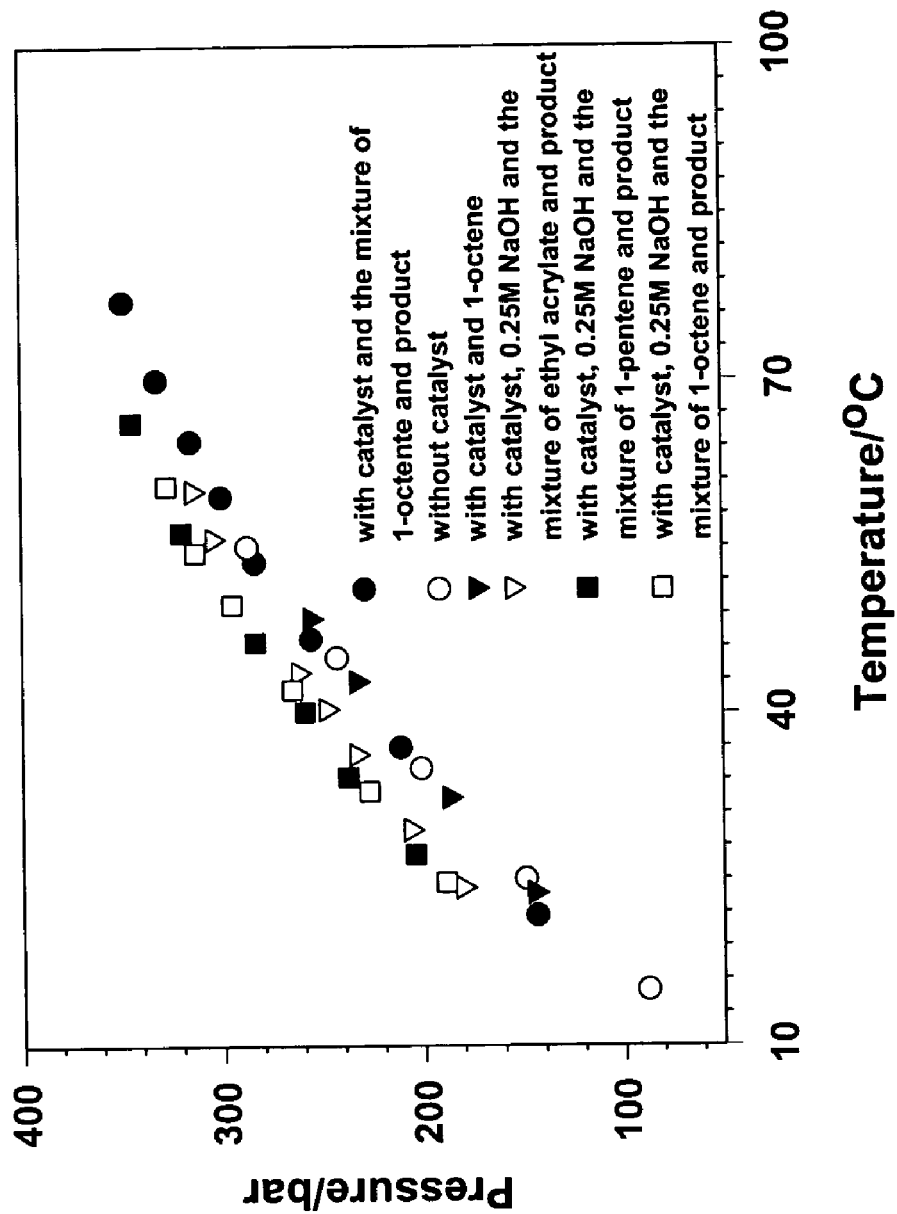
FIG. 2 is a plot of cloud point pressure versus temperature for several microemulsion systems.

FIG. 2 is a plot of cloud point pressure versus temperature for several microemulsion systems prepared according to the method of Example 1–5. The cloud point pressures increased with increasing temperature. The cloud point pressures were insensitive to the presence of catalyst in the water droplets and the presence of olefin and synthesis gas in the continuous carbon dioxide phase. There was a slight increase in cloud point pressure at lower temperatures when 0.25 M sodium hydroxide solution was substituted for pure water.

The examples demonstrate that reactions catalyzed by water-soluble organometallic catalysts can be carried out in a water-densified fluid microemulsion system.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. A catalytic process, comprising:
   reacting a reactant with an organometallic catalyst to form a product in a microemulsion comprising the reactant and the organometallic catalyst, and further comprising water, a densified fluid, and a surfactant; wherein the microemulsion has a pH of about 2 to about 8; and
   separating the product from the microemulsion wherein the catalytic process comprises hydroformylation, hydrogenation or carbonylation and the reactant comprises hydrogen, carbon monoxide or a combination of hydrogen and carbon monoxide.

2. The catalytic process of claim 1, wherein the reactant comprises a compound that is a gas at 25° C. and one atmosphere.

3. The catalytic process of claim 1, wherein the reactant comprises a compound that is a liquid at 25° C. and one atmosphere.

4. The catalytic process of claim 1, wherein the reactant comprises olefinic unsaturation.

5. The catalytic process of claim 1, wherein the reactant comprises a compound that is a solid at 25° C. and one atmosphere.

6. The catalytic process of claim 1, wherein the reactant comprises a compound that is a liquid at 25° C. and one atmosphere and a compound that is a gas at 25° C. and one atmosphere.

7. The catalytic process of claim 1, wherein the organometallic catalyst has a water solubility of at least about 0.001 gram per liter at 25° C. and one atmosphere.

8. The catalytic process of claim 1, wherein the organometallic catalyst comprises a metal selected from the group consisting of Mg, Al, Ca, Sc, Ti, V, Cr, Mn, Fe, Co, Ni, Cu, Zn, Ga, Ge, Sr, Y, Zr, Nb, Mo, Tc, Ru, Rh, Pd, Ag, Cd, In, Sn, Ba, La, Ce, Pr, Nd, Pm, Sm, Eu, Gd, Tb, Dy, Ho, Er, Tm, Yb, Lu, Hf, Ta, W, Re, Os, Ir, Pt, Au, Hg, Tl, Pb, Ra, Ac, Th, Pa, and U.

9. The catalytic process of claim 1, wherein the organometallic catalyst comprises a metal selected from the group consisting of Y, Zr, Nb, Mo, Tc, Ru, Rh, Pd, Ag, La, Hf, Ta, W, Re, Os, Ir, Pt, and Au.

10. The catalytic process of claim 1, wherein the organometallic catalyst comprises rhodium.

11. The catalytic process of claim 1, wherein the organometallic catalyst comprises a phosphine ligand having a water solubility of at least about 0.1 gram per liter at 25° C. and one atmosphere.

12. The catalytic process of claim 1, wherein the organometallic catalyst comprises a ligand selected from the group consisting of sulfonated aryl phosphines, trialkylammoniumalkyl phosphines, phosphines containing carboxylated aromatic groups and/or side chains, phosphines containing carboxyalkyl groups, hydroxyalkyl-substituted phosphines, trialkylammoniumalkyl-substituted phosphines, phosphines containing phosphonated aromatic groups and/or side chains, carboxy-substituted bipyridines, sulfonate-substituted bipyridines, sulfonated chiral phosphines, carboxy-substituted cyclopentadienes, and mixtures thereof.

13. The catalytic process of claim 1, wherein the organometallic catalyst has a molecular weight less than or equal to 5,000 atomic mass units.

14. The catalytic process of claim 1, wherein the surfactant comprises a perhalogenated surfactant, a propylene glycol surfactant, a perhaloether surfactant, a polydimethylsiloxane surfactant, or a mixture thereof.

15. The catalytic process of claim 1, wherein the surfactant comprises a salt of a fluorinated poly(ether)carboxylate or a fluorinated poly(ether)sulfonate.

16. A catalytic process, comprising:
reacting a reactant with an organometallic catalyst to form a product in a microemulsion comprising the reactant and the organometallic catalyst, and further comprising water, a densified fluid, and a surfactant; wherein the surfactant comprises sodium bis(3,3,4,4,5,5,6,6,7,7,8,8,8-tridecafluorooctyl)-2-sulfosuccinate, sodium bis(2,2,3,3,4,4,5,5-octafluoro-1-pentyl)-2-sulfosuccinate, sodium bis(2,2,3,4,4,4-hexafluorobutyl)-2-sulfosuccinate, or a mixture thereof; and
separating the product from the microemulsion wherein the catalytic process comprises hydroformylation, hydrogenation or carbonylation and the reactant comprises hydrogen, carbon monoxide or a combination of hydrogen and carbon monoxide and the microemulsion has a pH about 2 to about 8.

17. A catalytic process, comprising:
reacting a reactant with an organometallic catalyst to form a product in a microemulsion comprising the reactant and the organometallic catalyst, and further comprising water, a densified fluid, and a surfactant; wherein the surfactant comprises a fluorinated analog of sodium bis(2-ethylhexyl)-2-sulfosuccinate in which at least one hydrogen atom is replaced by a fluorine atom; and
separating the product from the microemulsion wherein the catalytic process comprises hydroformylation, hydrogenation or carbonylation and the reactant comprises hydrogen, carbon monoxide or a combination of hydrogen and carbon monoxide and the microemulsion has a pH about 2 to about 8.

18. The catalytic process of claim 1, wherein the densified fluid is a supercritical fluid having a critical temperature less than or equal to 31° C.

19. The catalytic process of claim 1, wherein densified fluid is a supercritical fluid having a critical pressure less than or equal to 7.4 megapascals.

20. The catalytic process of claim 1, wherein the densified fluid comprises carbon dioxide, ethane, propane, ethylene, propylene, nitrous oxide, or mixtures thereof.

21. The catalytic process of claim 1, wherein the densified fluid comprises carbon dioxide.

22. The catalytic process of claim 1, wherein the catalyzed reaction comprises hydroformylation.

23. The catalytic process of claim 1, wherein the microemulsion comprises aqueous emulsion particles having an average particle size less than or equal to 100 nanometers.

24. The catalytic process of claim 1, wherein the microemulsion comprises at least 1 weight percent water, based on the total weight of the microemulsion.

25. The catalytic process of claim 1, wherein forming the microemulsion comprises adjusting temperature in the reactor.

26. The catalytic process of claim 1, wherein forming the microemulsion comprises adjusting pressure in the reactor.

27. The catalytic process of claim 1, further comprising adding a solvent to the reactor.

28. The catalytic process of claim 27, wherein the solvent has a water solubility less than or equal to 0.1 gram per kilogram water.

29. The catalytic process of claim 27, wherein the solvent has a water solubility of at least about 1 gram per kilogram water.

30. A catalytic process, comprising:
adding a reactant to a reactor containing water, an organometallic catalyst, and a surfactant;
adding a fluid to the reactor, wherein the fluid is capable of forming a densified fluid;
forming a water-in-densified fluid microemulsion in the reactor, wherein the microemulsion facilitates a catalyzed reaction of the reactant to form a product; and wherein the microemulsion has a pH of about 2 to about 8;
removing densified fluid from the reactor; and
removing product from the reactor wherein the catalytic process comprises hydroformylation, hydrogenation or carbonylation and the reactant comprises hydrogen, carbon monoxide or a combination of hydrogen and carbon monoxide.

31. A catalytic process, comprising:
1) charging a reactor with water, an organometallic catalyst, and a surfactant;
2) adding a reactant to the reactor wherein the reactant comprises hydrogen, carbon monoxide or a combination of hydrogen and carbon monoxide;
3) adding a fluid to the reactor, wherein the fluid is capable of forming a densified fluid;
4) forming a water-in-densified fluid microemulsion in the reactor, wherein the microemulsion facilitates a catalyzed reaction of the reactant to form a product; and wherein the microemulsion has a pH of about 2 to about 8;
5) removing densified fluid from the reactor;
6) removing the product from the reactor; and
7) repeating steps 2) to 6) wherein the reactant comprises hydroformylation, hydrogenation or carbonylation.

32. A catalytic process, comprising:
reacting an olefin, hydrogen, carbon monoxide, and an organometallic catalyst comprising rhodium and trisodium 3,3',3"-phosphinidynetris(benzenesulfonate) in a microemulsion further comprising water, a densified fluid, and a surfactant to form a hydroformylation product; and
separating the hydroformylation product from the microemulsion.

33. A catalytic process, comprising:
reacting a reactant with an organometallic catalyst to form a product in a microemulsion comprising the reactant and the organometallic catalyst, and further comprising water, densified carbon dioxide, and a surfactant; wherein the microemulsion has a pH of about 2 to about 8; and separating the product from the microemulsion wherein the catalytic process comprises hydroformylation, hydrogenation or carbonylation and the reactant comprises hydrogen, carbon monoxide or a combination of hydrogen and carbon monoxide.

34. The catalytic process of claim 33, wherein the microemulsion has a pH of about 3 to about 8.

35. The catalytic process of claim 33, wherein the microemulsion has a pH of about 4 to about 8.

36. A catalytic process, comprising:
reacting an olefin, hydrogen, carbon monoxide, and an organometallic catalyst in a microemulsion further comprising water, densified carbon dioxide, and a surfactant to form a hydroformylation product; wherein the microemulsion has a pH of about 2 to about 8; and separating the hydroformylation product from the microemulsion.

37. The catalytic process of claim 36, wherein the microemulsion has a pH of about 3 to about 8.

38. The catalytic process of claim 36, wherein the microemulsion has a pH of about 4 to about 8.

39. A catalytic process, comprising:
1) charging a reactor with an organometallic catalyst, and an aqueous phase comprising a base;
2) adding a reactant to the reactor wherein the reactant comprises hydrogen, carbon monoxide or a combination of hydrogen and carbon monoxide;
3) adding a fluid to the reactor, wherein the fluid is capable of forming a densified fluid, and wherein the fluid comprises carbon dioxide;
4) forming a water-in-densified fluid microemulsion in the reactor, wherein the microemulsion facilitates a catalyzed reaction of the reactant to form a product; and wherein the microemulsion has a pH of about 2 to about 8;
5) removing densified fluid from the reactor;
6) removing the product from the reactor; and
7) repeating steps 2) to 6) wherein the catalyzed reaction comprises hydroformylation, hydrogenation or carbonylation.

40. The catalytic process of claim 39, wherein the microemulsion has a pH of about 3 to about 8.

41. The catalytic process of claim 39, wherein the microemulsion has a pH of about 4 to about 8.

* * * * *